United States Patent [19]

Kelly et al.

[11] Patent Number: 4,884,512
[45] Date of Patent: Dec. 5, 1989

[54] PLATE STABILIZER

[76] Inventors: Carol Kelly; Linda Herrington, both of 1963 Parker Rd., Perrysburg, N.Y. 14129

[21] Appl. No.: 276,904

[22] Filed: Nov. 28, 1988

Related U.S. Application Data

[63] Continuation-in-part of Ser. No. 43,368, Apr. 28, 1987, abandoned.

[51] Int. Cl.4 .............................................. A47B 85/00
[52] U.S. Cl. ...................................... 108/26; 108/25; 108/97
[58] Field of Search .................. 108/26, 25, 42, 97, 108/98, 65, 90, 44, 45; 206/562, 563, 564; 248/231.4, 287, 149

[56] References Cited

U.S. PATENT DOCUMENTS

| | | | |
|---|---|---|---|
| 1,242,785 | 10/1917 | Eldridge | 108/25 |
| 2,684,110 | 7/1954 | Stone | 108/26 X |
| 2,865,697 | 12/1958 | Staley | 108/25 |
| 2,935,209 | 5/1960 | Fritz | 108/25 |
| 4,319,727 | 3/1982 | Rattay | 248/149 |

Primary Examiner—Kenneth J. Dorner
Assistant Examiner—José V. Chen
Attorney, Agent, or Firm—James J. Ralabate

[57] ABSTRACT

A plate stabilizing device for fitting on a table or tray. The device has a tray section with a cut out portion for holding a dish. The device can accommodate various size dishes by means of grooves with different diameters. The device also can be used on tables or trays of varying thicknesses since it has an adjustable bracket means which fixes on to the table or tray.

9 Claims, 2 Drawing Sheets

PLATE STABILIZER

This application is a continuation in part application of parent application Ser. No. 07/043,368 filed Apr. 28, 1987 now abandoned. This invention relates to a plate-holding means and, more specifically, to a plate stabilizing device that is adapted to be attached to a table or the like.

BACKGROUND OF THE INVENTION

There is a present need for feeding devices useful for those individuals physically or mentally handicapped. People who have behavior disorders commonly will cause plates to fall off or slide from the tray or table supporting said plate. Also, patients with muscle tone or other physical problems sometimes cannot coordinate their eating efforts properly and cause the plate to move during their meal. Any type of patient that is physically restricted either temporarily or permanently needs assistance at times including in public places such as restaurants. People who have had heart attacks or strokes, or have MS usually need assistance from someone else when eating. It is important, however, to these people that when in public they draw as little attention to themselves as possible. In teaching these handicapped people to improve their eating skills or even just to permit them to eat properly along, a plate stabilizer means must be used.

There have been several attempts to provide devices for this use. Some contain suction cups at the bottom of the plate surface for attachment to the tray or table. These type devices easily become dislodged and cause the plate to slip off the tray. Other devices contain non-skid surfaces to prevent sliding of the plate but also with these the plates can easily be knocked off the tray by the impaired patient.

Some of the devices considered by others to assist in stabilizing plate-feeding means include those of U.S. Pat. Nos. 1,242,785; 2,517,018; 2,684,110; 2,697,574; 2,865,697 and 3,148,636. In U.S. Pat. No. 1,242,785 (Eldridge) a childs' highchair device is disclosed wherein a spring clamp is disposed below the device for spring-locking onto the highchair tray. The device of Eldridge has a recess or opening on its upper face to receive a plate or a cup. The plate or cup, however, can be easily dislodged since nothing holds the plate securely to the casting or plate holder. In the alternative, Eldridge suggests that the recess on the face of the device can be used itself as the container for food. This could present some problems associated with the cleanliness of the food receptacle. The entire element of Eldridge must be washed and cleaned as a unit making it awkward because of size and difficulty in reaching all parts of the food container. Also, washing a unit with part metal components could cause rusting and other impurities to contact the food compartment.

In U.S. Pat. No. 2,517,018 a dish fastener for dining tables is disclosed. In this patent to Nicholson snap fastener means are positioned at the bottom of each plate which in turn snaps and mates with a snap opening in a table. This device has not received large scale commercial use since it is not adapted for use with conventional tables or trays without snap-receiving members. While the locking means disclosed by Nicholson prevents lateral movement of the dish, it would be easy for a patient to pick up and throw the dish, or alternatively, accidentally dislodge the dish. Nicholson's device is specifically designed for small dishes such as butter dishes and designed for use with special table tops with snap-receiving members.

In U.S. Pat. No. 2,684,110 a baby chair with a locked-in food dish is disclosed. In this patent to Stone a locking mechanism is located below and in the underside of the chair tray. A latch device in the dish extends downward into the locking mechanism of the tray and secured thereto. This device is only usuable with a specifically designed baby's highchair with specifically equipped locking means. It is not adaptable to be used with any eating surface such as a table, tray, or other surfaces not specially made to receive the latch or lock of the dish. A more universal and versatile plate or dish-stabilizing means is desirable.

U.S. Pat. No. 2,697,574 to Bricker discloses a folding stand for supporting food plates or trays. This type of plate support can be easily knocked over by the mentally or physically handicapped. When in use a desirable aspect of a plate-stabilizing means includes its ability to maintain its usuable position and that of the plate. While Bricker locks his plate in place to secure it, the holder (or stand) for the plate is not secure. Thus, the total means are not appropriate for use by the handicapped patient or person. Bricker's support, however, is not intended for use by the handicapped but rather for those who have no problem with their eating skills.

In Staley, U.S. Pat. No. 2,865,697, a highchair tray having anchoring means for the plate is described. A spring-loaded bracket-locking means is disclosed which encloses a plate and then is locked within the bracket. The locking or plate-securing mechanism is only adapted to be used with specially designed chairs or eating trays for infants. Staley's invention includes a table assembly which is part of a highchair or infant's feeding table. The assembly has a recess to hold a plate and a releasable locking means which cooperates with this assembly. The releasable locking means is mounted within the table assembly and thus cannot be used except with that table assembly.

Lastly, U.S. Pat. No. 3,148,636 to Bloomquist et al discloses a serving tray having movable tabs that secure different size dishes in recesses in the tray. The entire tray or dish can be easily overturned in this type device but Bloomquist's device was only intended for disposable use for institutional meal service and not for use by those who require special treatment or accommodation during meals.

A device therefore for use by people with physical or mental problems, i.e. one arm or hand, or by someone with a stroke affecting their hand movement or someone with behavior problems is presently lacking in the prior art.

SUMMARY OF THE INVENTION

It is therefore an object of this invention to provide a plate-stabilizing means devoid of the above-noted disadvantages.

Another object of this invention is to provide a versatile, relatively simple and portable plate-stabilizing Still another object of this invention is to provide a plate-stabilizing means uniquely adapted for use by the handicapped.

Another still further object of this invention is to provide a plate support and stabilizing structure that is easy to clean, disinfect and maintain in a sanitary condition.

A further object of this invention is to provide a plate-stabilizing means that can conveniently be used with most any table top, wheel chair tray or other flat surface of any thickness.

Still a further object of this invention is to provide a plate-stabilizing means wherein the entire structure including the plate is substantially stable.

A further object is to provide a plate-stabilizing means that is convenient and easy to attach and remove.

These and further objects are accomplished by this invention generally speaking by a plate-stabilizing means having a substantially flat retainer tray means with a cut out section to permit exposure of the upper portion of a plate. A groove conforming to the configuration of a plate is provided in the thickness of the retainer tray. A plate is then slid into the groove wherein the outer periphery of the plate is securely fit into the tray. The food-containing portion of the plate is exposed through the cut out section for easy use and access. Extending from the back portion of the tray and fixed thereto is a clamp-holding means for attachment or securing to a flat surface such as a table top, tray or other support. The clamp or holding means is adjustable to accommodate various thickness of the table top, tray counter or other surface used. The clamp can be laterally adjustable to be used on any width support or can be downwardly adjustable to accommodate various thicknesses in the support. This feature will be further defined in reference to the drawings. The structure therefore, involves the use of a solid frame or tray portion constructed to allow a plate to be slid into the cut out area and lock therein. The extending clamp portion bends over the edge of a table or other surface to stabilize the unit. It can be constructed of polyethylene, or other unbreakable polymeric inert and non-toxic materials. It has no detachable parts except for the plate and is thus easy to carry, use and clean. It can be taken to a restaurant and easily placed on any table without drawing any significant attention to it. This is possible because of its relatively small size and its ease of setting up for use. Also, it will fit on most any surface irrespective of the width or thickness of the surface. By locking the plate or dish in the grooves of the tray and attaching the clamp to a secure surface, the plate is secured in place and cannot be dislodged or overturned easily. Also important is that the holding device of this invention will restrict movement of the plate or dish during eating.

DETAILED DESCRIPTION OF THE DRAWING AND PREFERRED EMBODIMENT

Figure 1:
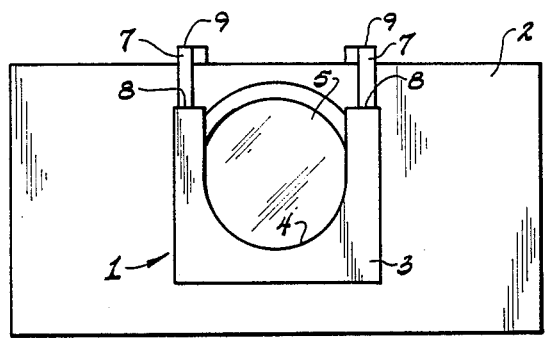
FIG. 1 is a top plan view of the plate stabilizer of this invention when attached to a tray or table surface.

In FIG. 1 plate stabilizer 1 is shown as it is attached to a tray or table surface 2. Usually, the stabilizer 1 will be attached to a tray such as a tray 2 but it can be secured to any flat surface. Stabilizer 1 comprises a tray section 3 having a half-circle cut out portion 4 into which a food-containing means or plate 5 will slide or fit in a fixed position. In the thickness of tray section 3 is at least one groove (12, 13 and 14 of FIG. 4) into which the periphery (or rim 15) of plate 5 slides. Once plate 5 is fit into the groove 6 (see FIG. 2) of cut out portion 4 the user cannot overturn the plate 5 or drop it or throw it, etc. Stabilizer 1 can be laterally adjusted by arms 7 to any size or width surface 2, or vertically adjusted by adjuster for any thickness or surface 2. Arms 7 laterally telescopically extend from the terminal ends 8 of tray section 3 and arms 7 can be pulled out to any width required. The tray section 3 can have recesses if desired for cups or glasses or the like. Plate 5 can easily be pulled out from grooves 6 to put food inplate or to clean plate 5. End pieces 9 and adjusting means 11 form a bracket that is u-shaped (see FIG. 4) and fit into the thickness of surface 2 to hold the stabilizer 1 firmly in position. These brackets can be adjustable as shown in FIG. 5 if required to accommodate various thicknesses of surface 2. Tray section 3 can be of any suitable configuration such as square as shown or circular depending upon the need or requirements of the use. The entire unit stabilizer 1 can be constructed of polystyene or other suitable non-toxic and washable material. It is important that the material used be capable of being machine washed since most institutions utilize dishwashers and other automatic equipment.

Figure 2:
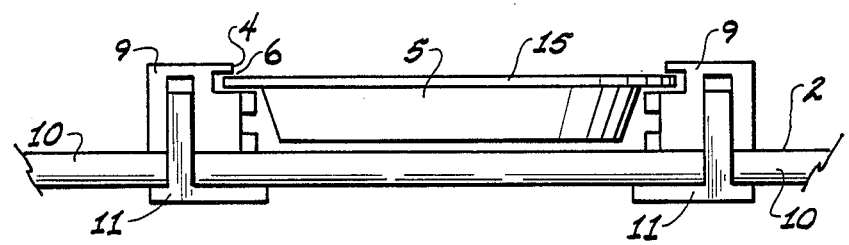
FIG. 2 is a rear edge view of the plate stabilizer of this invention when attached to a tray or table surface.

In FIG. 2 a rear edge view of the stabilizer 1 with plate 5 in position is illustrated. End piece 9 and adjusting means 11 form brackets which loop under and enclose the thickness portion 10 of surface 2 thus holding the stabilizer 1 in fixed position. These u-shaped formed holding means or brackets fit and lock easily around surface 2 providing both the plate 5 and tray 3 with stability. Semi-circle cut out 4 provides an opening for the upper surface of plate 5 to be available for feeding and containing food. These holding means can be adjusted by any suitable adjusting means such as an inverted t-shaped adjusting means 11 as shown in FIGS. 2 and 5. This adjuster 11 can be pulled downward and locked in place to accommodate, together with end piece 9, any thickness of surface 2. It can be locked in place by any known and available means such as a spring-loaded latch. Rim or peripheral portion of plate 5 slides into and is contained in grooves 12, and 14 as shown in FIG. 5.

Figure 3:
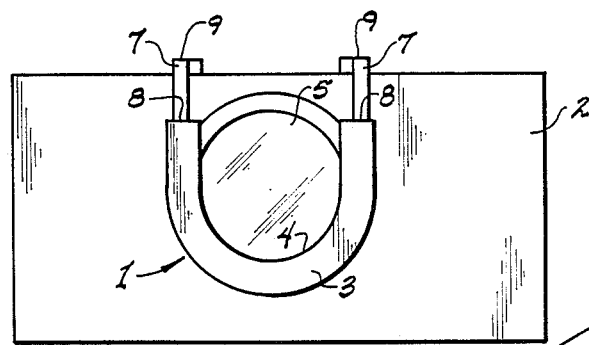
FIG. 3 is a top plan view of an embodiment of this invention.

In FIG. 3 the same stabilizer 1 is shown with, however, a circular tray portion 3 rather than the squared tray of FIG. 1. All other aspects of stabilizer 1 are as shown in the other figures.

Figure 4:
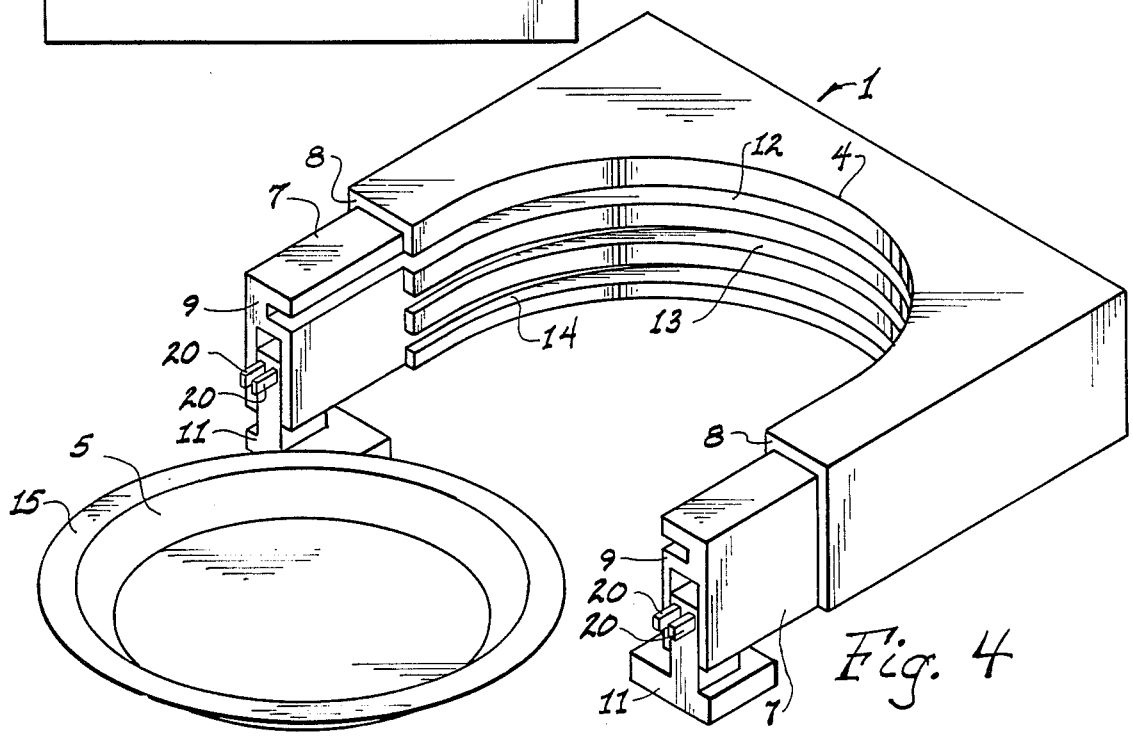
FIG. 4 is a perspective view of the plate section with adjuster opened.
Figure 5:
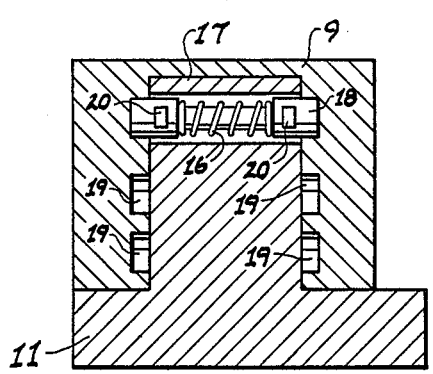
FIG. 5 is an expanded rear edge view of the plate stabilizer showing the vertically adjustable clamp or tray holders with in the closed position.

In FIG. 4 the stabilizer 1 is shown having plate 5 removed therefrom. Cut out portion 4 can have a series of grooves such as 12, 13 and 14 to accommodate and receive various diameter size plates 5. The groove with the smallest diameter can be located at the bottom as shown in 14 and the semi-circular groove with the largest diameter can be located at the top of cut out 4 as that groove shown at 12. Thus, plates with different size diameters or circumferences can be accommodated in stabilizer 1. Obviously, if only one size plate is desired, only one groove need be put in stabilizer 1. The size of each groove approximates the arc of at least one half of plate 5 but any other convenient arrangement can be used. Plate 5 should be constructed also of non-toxic, non-breakable material that can easily be washed and continuously used. Plate 5 has an extending rim 15 which slides into grooves 12, 13 and 14. While it is preferred that reusable plates 5 be used, it is within the scope of this invention to use disposable plates if they are strong enough and have a rim 15 that can fit into grooves 12, 13 and 14. Adjuster 11 is shown open whereas FIGS. 5 and 7 show adjuster 11 in its closed position.

Figure 8:
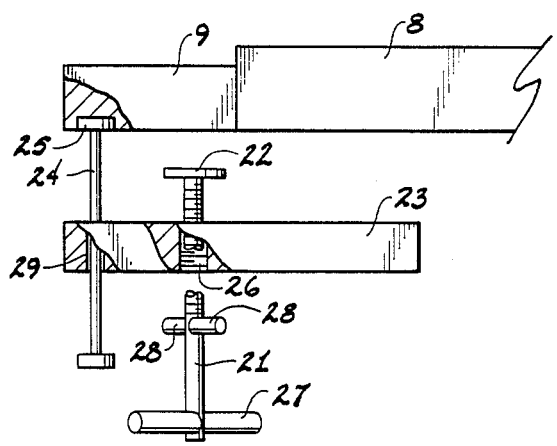
FIG. 8 is an alternative type adjusting means to the type shown in FIGS. 4, 5 and 6.

In FIG. 5 a vertically adjustable means 11 is illustrated. However, the invention is not limited to this type adjusting means. Any known or convenient adjusting means may be used to move stem 17 and adjusting means 11 up or down. Two known adjusting means are shown in FIGS. 5 and 8. In this embodiment, an inverted T-shaped slide means or adjuster 11 is shown where the stem 17 easily slides up and down a conduit in end pieces 9. Positioned in stem 17 is a spring-loaded latch means 18 that has latches 18 that can fit into mating apertures 19 in end piece 9 to lock into the desired width. Inverted T-shaped adjuster 11 is also shown detached from end piece 9 for clarity. Latches 18 can be protruding outward from stem 17 and can be locked in position by spring 16 which exerts an outward force on latches 18. Finger pinch pieces 20 are shown for pinching latches 18 inwardly to move adjuster 11 up or down to accommodate the desired width of surface 2. Inverted T-shaped adjuster 11 has a vertical stem 17 that houses spring means 16 and latches 18.

Figure 6:
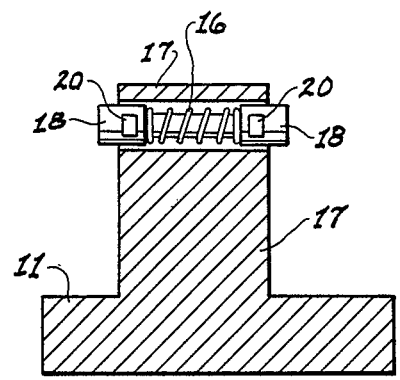
FIG. 6 is also an expanded view of the rear edge showing adjusting means 11 removed from end piece 9.
Figure 7:
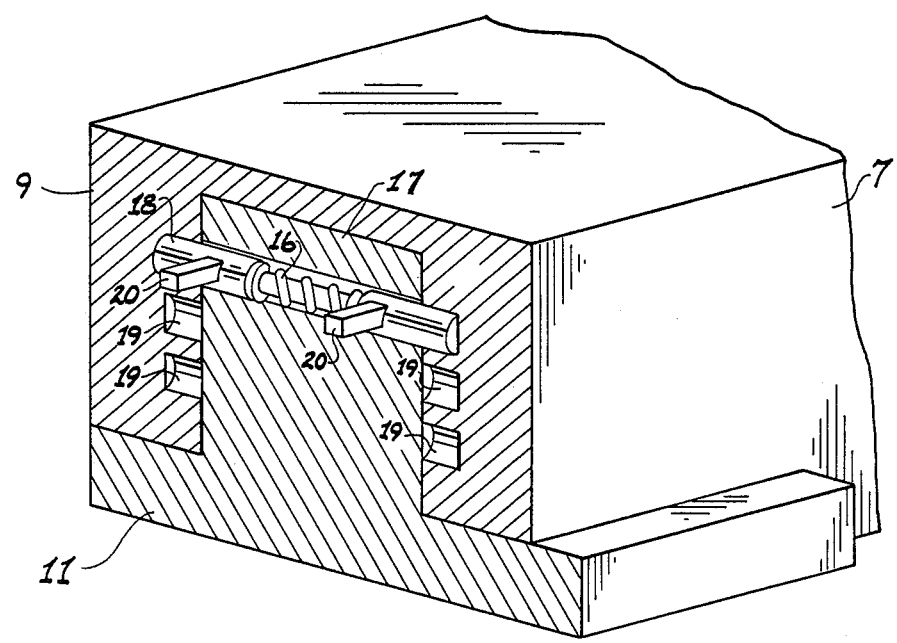
FIG. 7 is a perspective view of the rear edge of the plate stabilizer.

In FIG. 7 a side view of vertically adjustable means 11 is shown wherein finger pinch pieces extend outward from the stem 17 so as to be available for the user to pinch together and therefore move stem 17 up or down to accommodate the desired width of surface 2. When pieces 20 are pinched together, it pulls latches 18 out of apertures 19 and permits free up or down movement of stem 17. When finger pieces 20 are released they cause latches 18 which are spring loaded to snap back into the adjacent apertures 19 (as shown in FIG. 5 and FIG. 6) Apertures 19 are located in end piece 9 in vertical alignment in a plurality of positions to permit accommodation to any thickness of surface 2. Again to move stem 17 up or down, the user merely pinches outwardly projecting finger pinchpieces together, thus releasing spring-loaded latch means 18 from apertures 19 and permit up or down movement of stem 17 and base adjusting element 11 which is connected to stem 17.

In FIG. 8, an alternate adjusting means is shown that is a conventional turn screw 21 that has a circular plate 22 attached at its inner terminal portion. Base adjusting element or jaw 23 is freely movable, connected to end piece 9 by bolt 24. Bolt 24 is fixed to end piece 9 by head 25 and extends through an aperture 29 in jaw 23, and is freely movable therethrough. When handle piece 27 in screw 21 is turned, threaded screw 21 will move through threaded aperture 26 and will move jaw 23 and/or plate 22 up or down to tighten around the bottom portion of a surface 2. This type of tightening means is similar to that used on a vise or other known screw tightening devices. Since other tightening means or adjusting means as noted above can be used, those adjusting means of FIGS. 5 and 8 are merely shown as illustrative of means available to be used.

In FIG. 8, if screw projections 28 hit or contact jaw 23, it will move the entire jaw 23 upward upon tightening or turning of screw 21 through threaded aperture 26. Applicants' adjusting means however are not limited to those shown in FIGS. 5 and 8, these are merely shown for illustrative purposes. Any suitable adjusting means may be used.

The preferred and optimumly preferred embodiments of the present invention have been described herein and shown in the accompanying drawing to illustrate the underlying principles of the invention, but it is to be understood that numerous modifications and ramifications may be made without departing from the spirit and scope of this invention.

What is claimed is:

1. A plate stabilizing means for fitting on a flat surface such as a table or the like, said plate stabilizing means comprising in combination a tray section, tray arms, bracket means, and a food containing means, said tray section having a cut out portion for retaining said food containing means, said food containing means comprising a plate having a rim which fits into at least one groove horizontally positioned in a thickness portion of said tray section, said tray section having said tray arms movably extending from its rear portion, said bracket means including means for locking and adjusting the bracket means so as to accommodate various size supporting tables, said bracket means positioned at terminal portions of said arms, said food containing means removably positioned in and from said groove in the thickness portion of said tray section.

2. A plate stabilizing means for fitting on a flat surface such as a table, said plate stabilizing means comprising in combination a tray section, tray arms, bracket means, and a food containing means, said tray section having a cut out portion for retaining said food containing means, said food containing means comprising a plate having a rim which fits into at least one groove horizontally positioned in a thickness portion of said tray section, said tray section having said tray arms movably extending from its rear portion, said bracket means movable downwardly and being lockable and adjustable so as to accommodate various size supporting tables, said brackets positioned at terminal portions of said arms, said food containing means removably positioned in and from said groove in the thickness portion of said tray section.

3. The plate stabilizing means of claim 2 wherein the outer periphery of said tray section is of a rectangular configuration.

4. The plate stabilizing means of claim 2 wherein the outer periphery of said tray section is of a circular configuration.

5. The plate stabilizing means of claim 2 wherein said brackets are vertically adjustable to accommodate thickness.

6. The plate stabilizing means of claim 2 wherein said tray section includes at least one groove on a plane in said tray section below an upper surface of said tray section.

7. The plate stabilizing means of claim 2 wherein said food containing means is a plate having a circumference slightly larger than a periphery of said cut out portion.

8. The plate stabilizing means of claim 2 wherein said cut out portion of said tray section includes along its periphery a plurality of grooves for receiving said food containing means.

9. A plate stabilizing means comprising a tray section, bracket means, and a removable food containing means, said tray section having a cut out portion with a substantially semi-circular configuration, said cut out portion being located between two arms which movably extend outwardly from the rear terminal portion of said tray section, at the ends of said two arms are bracket means adapted to slide around a flat supporting surface to secure said plate stabilizing means to said supporting surface, said brackets being u-shaped with the space between its legs being substantially equal to the thickness of said flat supporting surface and adapted to fit tightly thereon.

* * * * *